(12) United States Patent
Gondi et al.

(10) Patent No.: US 9,472,207 B2
(45) Date of Patent: Oct. 18, 2016

(54) PORTABLE ASSISTIVE DEVICE FOR COMBATING AUTISM SPECTRUM DISORDERS

(71) Applicants: Suhas Gondi, Chantilly, VA (US); Andrea Shao-Yin Li, Vienna, VA (US); Maxinder S. Kanwal, Vienna, VA (US); Corwin de Boor, Arlington, VA (US); Muthuraman Chidambaram, Gainesville, VA (US); Anand Prasanna, Woodbridge, VA (US); Jae Young Chang, McLean, VA (US); Benjamin L. Hsu, Herndon, VA (US)

(72) Inventors: Suhas Gondi, Chantilly, VA (US); Andrea Shao-Yin Li, Vienna, VA (US); Maxinder S. Kanwal, Vienna, VA (US); Corwin de Boor, Arlington, VA (US); Muthuraman Chidambaram, Gainesville, VA (US); Anand Prasanna, Woodbridge, VA (US); Jae Young Chang, McLean, VA (US); Benjamin L. Hsu, Herndon, VA (US)

(*) Notice: Subject to any disclaimer, the term of this patent is extended or adjusted under 35 U.S.C. 154(b) by 0 days.

(21) Appl. No.: 14/305,252

(22) Filed: Jun. 16, 2014

(65) Prior Publication Data

US 2014/0379352 A1    Dec. 25, 2014

Related U.S. Application Data

(60) Provisional application No. 61/927,586, filed on Jan. 15, 2014, provisional application No. 61/837,277, filed on Jun. 20, 2013.

(51) Int. Cl.
| | |
|---|---|
| *G10L 25/00* | (2013.01) |
| *G10L 25/63* | (2013.01) |
| *G09B 19/00* | (2006.01) |
| *G09B 5/04* | (2006.01) |
| *G10L 25/30* | (2013.01) |
| *G10L 25/27* | (2013.01) |
| *G06F 19/00* | (2011.01) |

(52) U.S. Cl.
CPC ............. *G10L 25/63* (2013.01); *G09B 5/04* (2013.01); *G09B 19/00* (2013.01); *G06F 19/3481* (2013.01); *G10L 25/27* (2013.01); *G10L 25/30* (2013.01)

(58) Field of Classification Search
USPC ............... 704/270–271, 246, 247, 251, 252
See application file for complete search history.

(56) References Cited

U.S. PATENT DOCUMENTS

| | | | |
|---|---|---|---|
| 7,451,079 B2 | 11/2008 | Oudeyer | |
| 7,487,094 B1 | 2/2009 | Konig et al. | |
| 8,669,864 B1* | 3/2014 | Tedesco et al. | 340/539.12 |
| 8,938,390 B2* | 1/2015 | Xu et al. | 704/245 |
| 2002/0194002 A1* | 12/2002 | Petrushin | 704/270 |

(Continued)

OTHER PUBLICATIONS

10 Things to Know About New Autism Data, Mar. 31, 2014, Retrieved Apr. 30, 2014 from Centers for Disease Control and Prevention website: http://www.cdc.gov/features/dsautismdata/, 4 pgs.

(Continued)

*Primary Examiner* — Leonard Saint Cyr
(74) *Attorney, Agent, or Firm* — Hunton & Williams LLP

(57) ABSTRACT

Exemplary embodiments include an assistive device to facilitate social interactions in autistic individuals by identifying emotions using a voice-detecting machine learning algorithm that extracts emotion content from an audio sample input and outputs the emotional content to a user through a device. This device may be a portable, concealable, real-time and automatic device that may receive and process an audio input. The audio input may be analyzed using a machine learning algorithm. The device may output the closest emotional match to the autistic user. The output may be tactile in nature such as a vibration pattern that is different for different identified emotions.

24 Claims, 9 Drawing Sheets

(56) References Cited

U.S. PATENT DOCUMENTS

| | | | |
|---|---|---|---|
| 2006/0122834 A1 | 6/2006 | Bennett | |
| 2007/0162283 A1* | 7/2007 | Petrushin | 704/255 |
| 2009/0191521 A1* | 7/2009 | Paul et al. | 434/169 |
| 2009/0208913 A1* | 8/2009 | Xu et al. | 434/169 |
| 2010/0233662 A1* | 9/2010 | Casper | 434/185 |
| 2011/0229862 A1* | 9/2011 | Parikh | 434/156 |
| 2011/0294693 A1* | 12/2011 | Hu | 506/9 |
| 2014/0052448 A1 | 2/2014 | Krishnan et al. | |

OTHER PUBLICATIONS

Autism Spectrum Disorder (ASD), Mar. 29, 2012, Retrieved Jun. 13, 2013, 6 pgs.

Autism Fact Sheet, National Institute of Neurological Disorders, NINDS and NIH, Apr. 16, 2014, 6 pgs.

Autism Spectrum Disorders in the Workplace, Jan. 22, 2013, Retrieved Jan. 12, 2014 form Boston University Faculty and State Assistance website: http://www.bu.edu/fsao/2013/01/22/autism-spectrum-disorders-in-the-workplace., 8 pgs.

Kelleher III et al., The Autistic Neuron: Troubled Translation, Elsevier Inc. Oct. 31, 2008, pp. 401-406.

Berkowitz, Barking Mad? Dog Collar 'Translates' Dog Barks, Aug. 6, 2009, Retrieved Aug. 23, 2012 from ABC News website: http://abcnews.go.com/Technology/story?id=8251582, 3 pgs.

Building GUIs with MatLab, The Language of Technical Computing , The Math Works, Inc., dated Jun. 1997, 88 pgs.

Busso et al., Analysis of Emotion Recognition Using Facial Expressions, Speech and Multimodal Information, Oct. 13-14, 2004, pp. 205-211.

NPL article titled: CDC estimates 1 in 68 children has been identified with autism spectrum disorder, Mar. 27, 2014, Retrieved Apr. 30, 2014, http://www.cdc.gov/media/releases/2014/p0327-autism-spectrum-disorder.html. 3 pgs.

Employment Research and Reports, Jun. 20, 2013, Retrieved Jan. 12, 2014 from National Autism Resource and Information Center website: http://autismnow.org/on-the-job/employment-research-and reports/, pp. 3.

Schuller, et al. The Interspeech 2009 Emotion Challenge, Institute for Human-Machine Communication, Technische Universität München, German, Chair of Pattern Recognition, Friedrich-Alexander University Erlangen-Nuremberg, Germany 2009, 4 pgs.

Myers et al., Management of Children with Autism Spectrum Disorders, dated Jun. 6, 2014 http://pediatrics.aappublications.org/content/120/5/1162.full.html. pp. 1162-1182.

Metz, et al. Fusion of Acoustic and Linguistic Speech Features for Emotion Detection, 2009 IEEE International Conference on Semantic Computing, Jun. 2009, pp. 153-160.

Mozumder, S. (2010) Inspired by I, Robot, Indian-American student bags top science prize in U.S. Rediff News. Retrieved from http://www.rediff.com/news/report/inspired-by-i-robot-indian-american-student-bags-top-science-prize-in-us/20101207.htm., 2 pgs.

Bauman, et al., Neuroanatomic observations of the brain in autism: a review and future directions, International Journal of Developmental Neuroscience, Nov. 23, 2005, pp. 183-187.

Eyben, et al., openSMILE, the Munich open Speech and Music Interpretation by Large Space, Extraction toolkit, Version 2.0.0, May 17, 2013, pp. 1-69.

Oudeyer, The Production and Recognition of Emotions in Speech: Features and Algorithms, Accepted Nov. 30, 2002, Elsevier Science Ltd., pp. 157-183.

Professional Experience, Worrying Experts, CBS News website: http://www.cbsnews.com/news/one-in-three-adults-with-autism-lack-professional-experience-worryint-experts/. dated Aug. 22, 2002, pp. 3.

Dai, et al., College of Computer and Information Science, Northeastern University, Boston, MA, Speech Technology and Applied Research, Bedford, MA, 2008, 6 pgs.

Schuller, et al., Hidden Markov Model-Based Speech Emotion Recognition, IEEE, Apr. 6-10, 2003, pp. 401-404.

Schuller, et al., Speech Emotion Recognition Combining Acoustic Features and Linguistic Information in a Hybrid Support Vector Machine—Belief Network Architecture, IEEE, dated 2004, pp. 577-580.

NPL article titled: Emotion Detection from Speech, 2007, 5 pgs.

Sociable Machines. (n.d.). Retrieved Jul. 12, 2012, from Kismet website: http://www.ai.mit.edu/projects/sociable/affective-intent.html. 4 pgs.

Takahashi, et al. Remarks on SVM-Based Emotion Recognition from Multi-Modal Bio-Potential signals, IEEE, Sep. 20-22, 2004, pp. 95-100.

Vosloo, J., Neuroplasticity and Autism, Retrieved Jul. 9, 2012, from Autism and Behavior website: http://www.autism-chatline.com.com/NEUROPLASTISITY-AND-AUTISM-, 2 pgs.

Wu, et al., Emotion Recognition from Speech Using IG-Based Feature Compensation, The Association for computational Linguistics and Chinese Language Processing, Oct. 10, 2006, pp. 65-78.

Zeidner, et al., Emotional Intelligence in the Workplace: A Critical Review, International Assoc. for Applied Psychology, 2004, pp. 371-399.

\* cited by examiner

PORTABLE ASSISTIVE DEVICE FOR COMBATING AUTISM SPECTRUM DISORDERS

CROSS REFERENCE TO RELATED APPLICATIONS

This application claims the benefit of U.S. Provisional Application No. 61/837,277, filed Jun. 20, 2013 and U.S. Provisional Application No. 61/927,586, filed on Jan. 15, 2014. The contents these provisional applications are hereby incorporated by reference in their entirety.

BACKGROUND

Autism spectrum disorders (ASDs) are brain development disorders that affect 1 in 68 children and result in an average spending of more than 6 times the cost in medical expenditures as compared with unaffected children according to the CDC. See Centers for Disease Control and Prevention. (2014 Mar. 24), Autism Spectrum Disorders Data and Statistics, available at http://www.cdc.gov/ncbddd/autism/data.html. ASDs disrupt basic prenatal and postnatal processes essential to the normal growth of the nervous system. Recent research has implicated a variety of neuroanatomical areas in the pathology of ASDs, including the cerebellum, hippocampus, and amygdala. See Bauman, M. L., & Kemper, T. L. (2005), Neuroanatomic observations of the brain in autism: a review and future directions, International Journal of Developmental Neuroscience, 23(2-3), 183-187.

Abnormalities in these and other areas result in deficiencies in cognition as well as perception and communication of emotions. More broadly, the National Institutes of Health define ASDs as "a range of complex neurodevelopment disorders, characterized by social impairments, communication difficulties, and restricted, repetitive, and stereotyped patterns of behavior." See Office of Communications and Public Liaison (2014, April), Autism Fact Sheet, available at: http://www.ninds.nih.gov/disorders/autism/detail_autism.htm. These symptoms greatly diminish the quality of life of afflicted individuals due to the resulting struggle to form meaningful relationships, and of caregivers who must cope daily with autistic individuals. A hallmark of ASDs is a difficulty with emotion recognition, which can create social barriers and hinder the formation of meaningful relationships.

Specifically, patients with ASD cannot understand emotions such as happiness, sadness, or anger from spoken voice, a basic process that usually occurs naturally in others without ASD. See Myers, S. M., & Johnson, C. P. (2007), Management of children with autism spectrum disorders, Pediatrics, 120(5), 1162-1182. To a large extent, this symptom alone prevents autistic individuals, notably children, from creating the emotional attachments that foment strong mental, intellectual, and emotional growth. In addition, this inability to read emotions detracts from much simpler everyday interactions by stifling communication. Current methods of treatment and remediation, particularly for children, include specialized education, behavior and social skills therapy, and placing affected individuals in highly structured environments, all of which have met with limited success. See Office of Communications and Public Liaison (2014, April), Autism Fact Sheet, available at: http://www.ninds.nih.gov/disorders/autism/detail_autism.htm. These approaches limit rather than enable the breadth of the child's interactions within the greater community. Furthermore, they are costly in time, effort, and dollars, demanding patience and draining energy from caregivers.

These and other deficiencies exist.

SUMMARY OF THE PREFERRED EMBODIMENTS

An exemplary embodiment includes a computer implemented method having steps including: receiving an audio input comprising spoken words; sampling the audio input into a sample of a predetermined length of time; processing the sample by application of an algorithm that determines emotional content of the sample; and outputting a closest emotional match to the emotional content of the sample.

In other exemplary embodiments, the preceding method may be performed using a system with a processor and a memory comprising computer-readable instructions which when executed by the processor cause the processor to perform the method steps.

Another exemplary embodiment includes an apparatus, including: a wearable device having a processor; and a memory comprising computer-readable instructions which when executed by the processor cause the processor to perform the following steps: receiving an audio input comprising spoken words through a microphone communicatively coupled to the processor; sampling the audio input into a sample of a predetermined length of time; processing the sample by application of an algorithm that determines an emotional content of the sample; and outputting a closest emotional match to the emotional content of the sample.

These and other embodiments and advantages of the invention will become apparent from the following detailed description, taken in conjunction with the accompanying drawings, illustrating by way of example the principles of the various exemplary embodiments.

DETAILED DESCRIPTION OF THE PREFERRED EMBODIMENTS

Figure 1A:
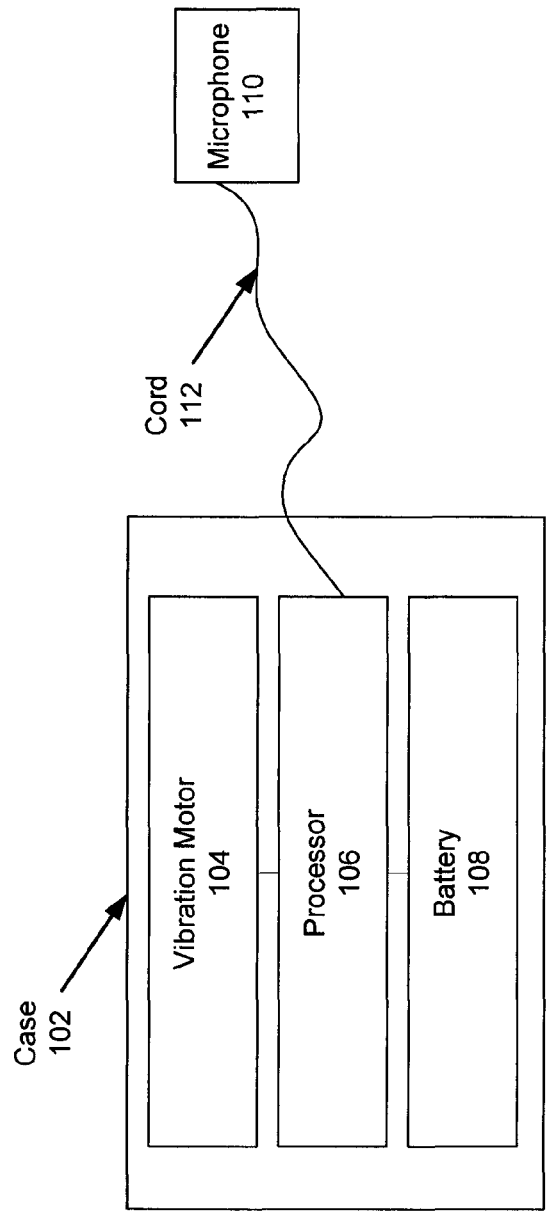
FIG. 1A depicts a first system in accordance with an exemplary embodiment.

It will be readily understood by those persons skilled in the art that the embodiments of the inventions described herein are capable of broad utility and application.

Accordingly, while the invention is described herein in detail in relation to the exemplary embodiments, it is to be understood that this disclosure is illustrative and exemplary of embodiments of the invention are described to provide an enabling disclosure of the invention. Accordingly, the disclosure is not intended to be construed to limit the embodiments of the invention or otherwise to exclude any other such embodiments, adaptations, variations, modifications and equivalent arrangements. The methods and systems described herein may be applied to other related services involving interaction with similar devices in other industries and services.

The following descriptions are provided of different configurations and features according to exemplary embodiments. While certain nomenclature and types of applications/hardware are described, other names and application/hardware usage is possible and the nomenclature provided is done so by way of non-limiting examples only. Further while particular embodiments are described, it should be appreciated that the features and functions of each embodiment may be combined in any combination as is within the capability of one of ordinary skill in the art. The attached Figures provide additional details regarding the present invention. It should also be appreciated that these exemplary embodiments are provided as non-limiting examples only.

In the Figures, while a single illustrative block, module or component is shown, these illustrative blocks, modules, or components may be multiplied for various applications or different application environments. In addition, the modules or components may be further combined into a consolidated unit. The modules and/or components may be further duplicated, combined and/or separated across multiple systems at local and/or remote locations. For example, some of the modules or functionality associated with the modules may be supported by a separate application or platform. Other implementations and architectures may be realized. It should be appreciated that embodiments described may be integrated into and run on a computer and/or a computing device (such as, for example, portable computing device), which may include a programmed processing machine which has one or more processors. Such a processing machine may execute instructions stored in a memory to process the data and execute the methods described herein.

Exemplary methods are provided by way of example herein, as there are a variety of ways to carry out the method disclosed herein. The methods depicted in the Figures may be executed or otherwise performed by one or a combination of various systems, such as described herein. Each block shown in the Figures represents one or more processes, methods, and/or subroutines carried out in the exemplary methods. Each block may have an associated processing machine or the blocks depicted may be carried out through one processor machine. Furthermore, while the steps may be shown in a particular order, it should be appreciated that the steps may be conducted in a different order.

As noted above, the processing machine executes the instructions that are stored in the memory or memories or persistent or non-transitory data storage devices to process data. This processing of data may be in response to commands by a user or users of the processing machine, in response to previous processing, in response to a request by another processing machine and/or any other input, for example. As described herein, a module performing functionality may have a processor.

The logic herein described may be implemented by hardware, software, and/or a combination therefor. In embodiments where the logic is implemented using software, upgrades and other changes may be performed without hardware changes. The software may be embodied in a non-transitory computer readable medium.

While the present invention has been described here in detail in relation to its exemplary embodiments, it is to be understood that this disclosure is only illustrative and exemplary of the present invention and is made to provide an enabling disclosure of the invention. Accordingly, the foregoing disclosure is not intended to be construed or to limit the present invention or otherwise to exclude any other such embodiments, adaptations, variations, modifications and equivalent arrangements.

Exemplary embodiments leverage the established potential for neural plasticity in the human brain. Exemplary embodiments further address deficiencies in the prior methods and systems for improving communication potential for persons with ASDs. Accordingly, exemplary embodiments can be utilized to improve communicative potential in persons, including children, suffering from ASDs. However, it should be appreciated that adults can benefit from exemplary embodiments.

Normal day-to-day conversations are not just words combined together to form sentences; rather, tone, mood, and intention contribute significantly to the meaning behind words in even the simplest conversations and interactions. This understanding of the intersection between emotion and spoken words comes relatively naturally to the average person. Unfortunately, the same cannot be said for individuals with ASDs.

ASDs affect one in 68 individuals with prevalence on the rise. Two of the most common clinical features include poor verbal communication skills and difficulty with identifying emotion and mood in a conversational setting. Such symptoms become impediments to the development of friendships, communication of needs, and expression of emotions and ideas. Miscommunication and frustration may often result, and weaker social skills and stifled emotional development may ultimately contribute to difficulties with entering the workforce later in life.

Just as a hearing aid or cochlear implant alleviates hearing loss, so too, an emotive aid can facilitate perception of emotions and stimulate communication. When made available at an early age, within the critical time window of development of the limbic brain (e.g., amygdala), this aid can improve the communicative potential for those diagnosed with ASDs. This benefit is analogous to the reduction in the propensity of congenitally deaf individuals to develop speech disorders if a cochlear-implant is used at an early age. As for deafness, the availability of an emotive aid provides the motivation for an early diagnosis and intervention for ASDs. Correspondence with caregivers and researchers supports the notion that an emotive aid such as the one proposed here could be very useful for autistic children struggling to have meaningful conversations and relationships. It should be appreciated that while exemplary embodiments are described in the context of ASDs, exemplary embodiments may have application to other developmental conditions that impact development of social skills and emotional intelligence.

Exemplary embodiments include an assistive device to facilitate social interactions in autistic individuals by identifying emotions using a voice-detecting machine learning algorithm that extracts emotion from voice and displays it to the user on a bracelet and/or outputs it to the individual through a vibratory pattern. This device may be known as the EmotivAid which is a portable, concealable, real-time and automatic device.

The EmotivAid works by first receiving audio input in two-second clips by the microphone, processing and analyzing the voice using a machine learning algorithm, and outputting the closest emotional match to the autistic user. During a conversation, the device continuously records two second bits of audio data and uses a previously-trained support vector machine (SVM) to classify the incoming samples in real time into emotional groups (e.g., neutral, happy, sad, or angry). It should be appreciated that these emotional groups are meant to be exemplary and non-limiting. When the emotion is identified, a vibration motor will send the user a simple but specific vibration pattern. This vibration pattern will indicate to the user which emotion is being expressed. The vibration pattern may be akin to a smart phone having different vibration patterns for a phone call vs. a text message, for example. The vibration pattern is used because autistic children are especially sensitive to touch. This aspect of the device enables more flexibility in the size of the invention (which can be placed in the user's pocket, on the wrist, clipped to the belt, etc.) as well as greater concealability.

A second computational component of exemplary embodiments may be an interactive GUI (Graphical User Interface), which outputs the resulting emotion on the wearable device in response to the emotion extraction algorithm. A circular memory buffer allows real-time processing of two-second speech segments without loss of information. The output may be associated with clear, user-friendly emoticons and/or tactile output. Voice analysis and output code may be embedded within a controller and fabricated to fit into a device that is small enough to make the system mobile. For example, the device may be a wearable device. For example, the device may be a bracelet or a pocket-sized device. The device may be equipped with an onboard, omnidirectional, miniature microphone, as well as amplifier and filters (e.g., a noise filter) to condition the sounds before analysis. In some embodiments the microphone may be external to the device.

A vibration can alert the wearer to attend to the speaker (person) initiating conversation. The device can recapture the emotions associated with different emotions within sounds to which the subject was exposed during training. The wearable device is powered by a source. The power source may be a battery or other suitable power source. The battery power source may be a replaceable battery. The battery may be rechargeable. In some embodiments, a hearing aid type battery (e.g., a 3V battery) may be used.

Extrapolating from the results of the neural network algorithms for emotion from speech extraction by Oudeyer, P. (2003), The production and recognition of emotions in speech: features and algorithms, *International Journal of Human-Computer Studies,* 59, 157-183 (the contents of which are incorporated by reference), a >93% accuracy is hypothesized with feature selection and training in our device. A full data analysis and statistics comparing the algorithm's efficacy against the more common Melfrequency Cepstral Coefficients-based approaches has been performed. Dai K., Fell H. J., MacAuslan J., Recognizing emotion in speech using neural networks, available at: http://www.ccs.neu.edu/home/daikeshi/papers/iasted08.pdf (the contents of which are incorporated by reference).

Feedback on the device was received from parents and caregivers of autistic individuals. Surveys with Likert scales may be employed to provide a quantitative measure of practical success. The wearable device, although aimed towards supplementing an ability that is deficient in autistics, may also have beneficial, and possibly therapeutic, effects from a biological standpoint. If used starting from a young age, the wearable device could promote the formation of associations between voice and emotion that are lacking due to the effects of autism. By repeatedly showing links between voice and emotion, the afflicted individual could begin to make these connections on their own after sufficient conditioning due to their neural plasticity.

Exemplary embodiments may also be implemented in a variety of manners. For example, various embodiments may be implemented in a mobile or portable device. For example, the implementation may be through an application or widget for a smart phone and/or a tablet computing device. Other embodiments may be implemented through a wearable device or other self-contained device that can be mounted or worn on a person. For example, the device may be a pocket-sized device that can be placed into a pants or shirt pocket and have a microphone that can be clipped or otherwise secured to the outside of the pocket or an alternate location. In some embodiments, the microphone may be internal to the device. Exemplary embodiments are desired to be located on the person such that the vibration can be felt by the person and the microphone is desired to be located such that audio content of speech is readily intercepted and recorded.

FIG. 1A depicts a system according to an exemplary embodiment of the invention. System 100 may provide various functionality and features associated with exemplary embodiments. More specifically, system 100 may include a case 102, vibration motor 104, processor 106, battery 108, microphone 110, and cord 112. As depicted in FIG. 1A, each of the components may be communicatively coupled. Moreover, it should be appreciated that the component arrangement depicted in FIG. 1A is meant to be exemplary and non-limiting.

The case 102 may contain the elements of the system 100. The case 102 may be plastic or another suitable lightweight material such as a composite or metal. The case 102 may be opaque. For example, the case 102 may be black. In various embodiments, the case 102 may be transparent. For example, the case 102 may be clear such that the internal components are visible through the case 102. In other embodiments, the case 102 may be other colors and/or a combination of opaque and transparent sections.

Within the case 102 may be a vibration motor 104, a processor 106, and a battery 108. The battery 108 may provide power to the system 100. It should be appreciated that while the battery 108 is depicted as being coupled to the processor 106, the battery 108 may also be coupled to the vibration motor 104. The battery may be a small, long-life battery. For example, the battery may be a hearing aid or watch type battery. In various embodiments, other types of batteries such as, for example, a 9-V battery or a rechargeable battery may be used. The rechargeable battery may be a 9-V battery. The case 102 may have an access to allow for the battery to be changed/replaced. In various embodiments, the battery may be external to the case 102. In these embodiments, the battery may be connected to the various components of the device either through a single connection or through multiple connections.

The processor 106 may be one or more computer processors. The processor 106 may include transitory computer readable storage and non-transitory computer readable storage. For example, the processor 106 may include Random Access Memory (RAM) and storage, such as solid state type storage, and a graphics processing unit. The processor 106 may be a motherboard or circuit board with various components. For example, the processor 106, according to exemplary embodiments may be a Raspberry Pi or similar processing device. The processor 106 may include ports or connection points for communicatively coupling with external devices.

The vibration motor may be actuated by the processor and be capable of causing a noticeable vibration of the case 102. The vibration may be in a specific pattern that is determined by the processor from a plurality of possible patterns. For example, different vibration patterns may represent different emotive states. The processor 106 may receive input from a microphone 110 that is coupled to the processor through a cord 112. In some embodiments, the cord 112 may be connected through a plug on the external surface of the case 102 that is coupled to the processor 106. The cord 112 may be removable. Likewise, in some embodiments, the microphone 110 may be removable from the cord 112. The cord 112 may be of varying length. In various embodiments, the microphone 110 may be a wireless microphone. For example, the microphone 110 may be a Bluetooth microphone.

In various embodiments, the processor 106 may include a sound card. The sound card may be integral to the processor 106. In some embodiments, the sound card may be communicatively coupled to the processor 106. For example, the sound card may be external to the processor 106. In various embodiments, the sound card may be external to the case 102. The cord 112 may be connected to or coupled with the sound card and the sound card may perform the processing of the received audio signal from the microphone.

As described above, the system 100 may be implemented using a Raspberry Pi. It should be appreciated that this is meant to be exemplary and non-limiting as other implementations are possible. This example is merely provided to depict one possible implementation according to exemplary embodiments. The Raspberry Pi was responsible for the processing and analysis of the audio samples. A Raspberry Pi is essentially a mini-computer on a board with independent processing power. This credit-card sized computer provides a fully functional version of Linux as well as a range of peripherals and a larger developer pool. This extensibility allows for the connection of different devices such as a microphone, screen, or vibration motor. In exemplary embodiments, a microphone and vibration motor can be attached to the Raspberry Pi to communicate the appropriate vibration pattern. The Raspberry Pi may be stored in a case which can be created with a 3D printer, and the entire device can be placed comfortably in a user's pocket. A small and inconspicuous microphone can be clipped to the outside of the user's pocket or collar or belt or other suitable location to receive two-second audio clips to be processed by the Raspberry Pi.

Figure 1B:
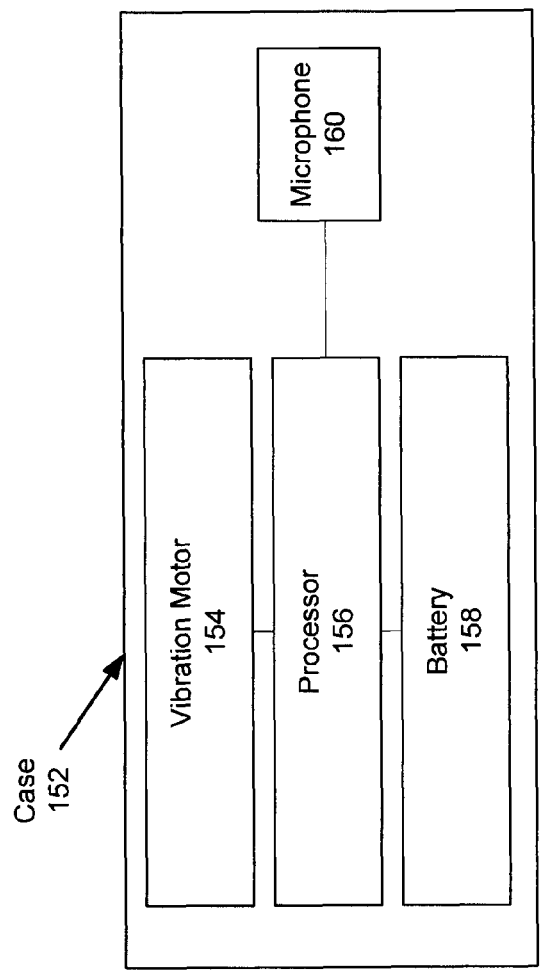
FIG. 1B depicts a second system in accordance with an exemplary embodiment.

FIG. 1B depicts a system according to an exemplary embodiment of the invention. System 150 may provide various functionality and features associated with exemplary embodiments. More specifically, system 150 may include a case 152, vibration motor 154, processor 156, battery 158, and microphone 160. As depicted in FIG. 1B, each of the components may be communicatively coupled. Moreover, it should be appreciated that the component arrangement depicted in FIG. 1B is meant to be exemplary and non-limiting.

The system 150 may have similar components to that of the system 100 as can be seen. However, the system 150 may have the microphone 160 located internal to the case 152. The system 150 may be implemented as a wearable device. For example, the wearable device may be a bracelet.

Figure 1C:
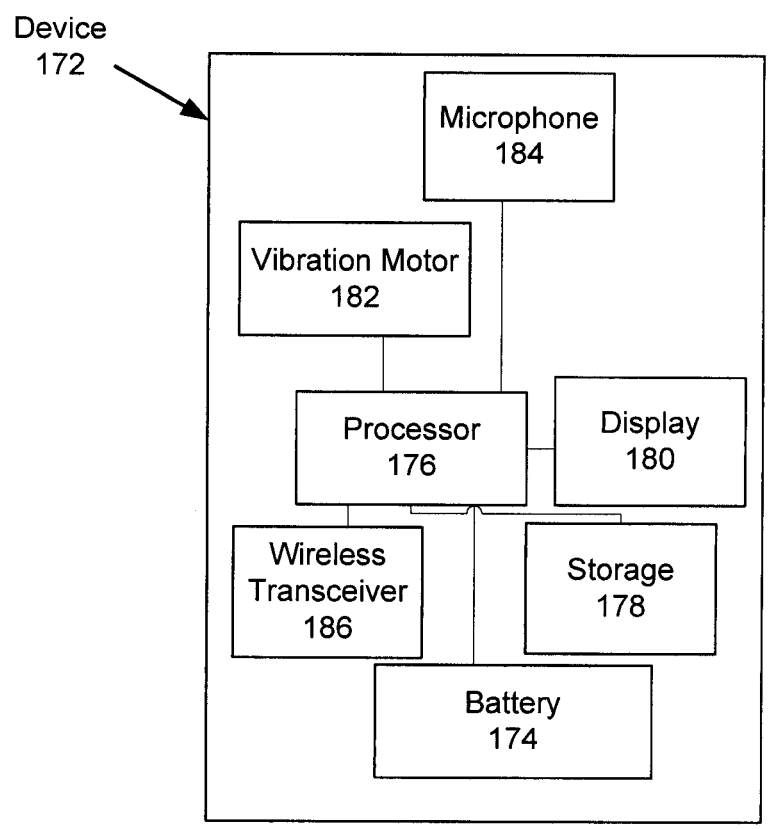
FIG. 1C depicts a third system in accordance with an exemplary embodiment.

It should be appreciated that the arrangement of the components in FIG. 1C is meant to be exemplary and non-limiting.

FIG. 1C depicts an exemplary embodiment of the system 170 implemented using a portable electronic device such as a smartphone or other similar device (e.g., a tablet computing device). An application or widget or other program can provide the processing logic and necessary algorithm. Utilizing an integrated microphone, a Bluetooth microphone, or a similar device communicatively coupled to the portable electronic device, the two-second sound samples can be temporarily recorded, then sent to a cloud-based processing and analysis system. This cloud-based system would implement the SVM and return the appropriate emotion classification to the smart device and user. This processing modality would allow for continuous updating of the SVM classifier and expansion of the emotion training database without any physical upgrade in the hardware of the end user's device. The system can use the vibration capability of the portable electronic device to provide output to the user.

The components depicted in FIG. 1C may be a part of the device 172. The device 172 may be a portable electronic device. For example, the device 172 may be a smart phone or tablet computing device or a personal digital assistant or the like. The device 172 may support the implementation of exemplary embodiments that make use of various components of the device 172. The device 172 may have a battery 174, a processor 176, storage 178, a display 180, a vibration motor 182, and a microphone 184. Program code may be loaded onto the device 172 and stored in the storage 178. The storage 178 may be a non-transitory computer readable medium. The program code may be in the form of an application. The program code may be executed by the processor 176. The application may be accessed by a user through the display 180. The display 180 may be a touch type display. Alternatively, the device 172 may have an input device such as a keyboard. A microphone 184 may be internal to the device 172. Alternatively, the microphone 184 may be external to the device 172 and communicatively coupled thereto. The program code may case the processor to cause the vibration motor 182 to vibrate in response to received audio from the microphone 184. In some embodiments, the expressed emotion can be communicated to the user through the display 180. A combination of output using the vibration motor 182 and the display 180 may be used.

The device 172 may further have a wireless transceiver 186. The wireless transceiver 186 may enable the device 172 to communicatively couple with a wireless network. The wireless network may be computer-based. For example, the wireless network may be a cellular network or an 802.11 type wireless network. Other types of wireless networks may be used. As noted above, the two-second sound samples can be temporarily recorded and stored in the device, then sent to a cloud-based processing and analysis system using the wireless transceiver. This cloud-based system would implement the SVM and return the appropriate emotion classification to the smart device and user. In this manner, the processing can be offloaded to a remote location. In should be appreciated that a combination of local and cloud-based processing may be used. For example, the device 172 may process the audio and provide the appropriate output and then transmit the audio to the cloud-based system. The device 172 may periodically receive updates from the cloud-based system.

It should be appreciated that the arrangement of the components in FIG. 1C is meant to be exemplary and non-limiting.

Furthermore, it should be appreciated that the cloud-based processing may be included in the embodiments depicted in FIGS. 1A and 1B by inclusion of a wireless transceiver in those embodiments. A display may also be included in the embodiments depicted in FIGS. 1A and 1B.

Figure 2:
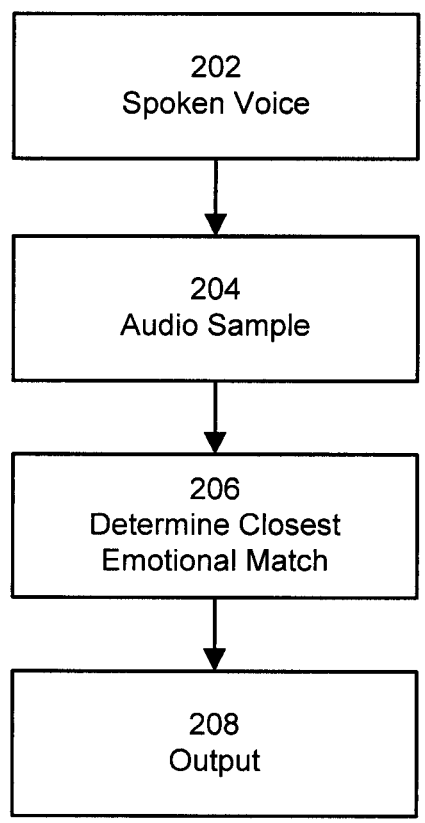
FIG. 2 is a flow chart of a method for providing an output corresponding to the emotional content of a real-time audio sample in accordance with an exemplary embodiment.

FIG. 2 depicts a flow chart of a method according to exemplary embodiments. Exemplary method 200 is provided by way of example, as there are a variety of ways to carry out the methods disclosed herein. The method 200 as shown in FIG. 2 may be executed or otherwise performed by one or a combination of various systems, such as a computer implemented system as described herein.

At block 202, a voice speaks. The speaking may occur in a conversation. The listener, according to exemplary embodiments, may be a person with an ASD(s). The listener may have a device as described herein. For example, the listener may have an EmotivAid that may be in one of the various embodiments described herein such as a wearable device (e.g., a bracelet or other device), a device in the listener's pocket, or an application on the listener's smart phone or similar portable computing device.

A block 204, an audio sample of the spoken voice is taken. The sample taken may be two to four seconds in length. It should be appreciated that other sampling lengths may be used. For example, a longer or shorter sampling length may be used. Thus, the audio sample may be a sound bite of the spoken voice or a subset of the conversation. The sample may be taken by a microphone or other listening device communicatively coupled to the device.

At block 206, the audio sample is processed by the device. The processing may include application of the algorithm according to exemplary embodiments. The algorithm determines the emotional tone and content of the audio sample.

At block 208, an output is made to the listener through the device. The output, according to exemplary embodiments, may be in the form of a vibration pattern that corresponds to the emotional tone and content of the audio sample. This output is made in real-time so that the output is received by the listener, who in conjunction with the spoken voice they have heard, can then respond properly to the speaker.

In various embodiments, the output may be visual in addition to or in lieu of a tactile (vibration) output. The visual output may be on a display and may be an emoticon or image that corresponds to the emotion type and content of the audio sample.

In various embodiments, if over a predetermined period of time, the same emotional content of the audio is detected, the vibration output may cease since continuous vibration may become annoying for the user. For example, the predetermined period of time may be 30 seconds. It should be appreciated that longer or shorter periods of time may be used.

Figure 3A:
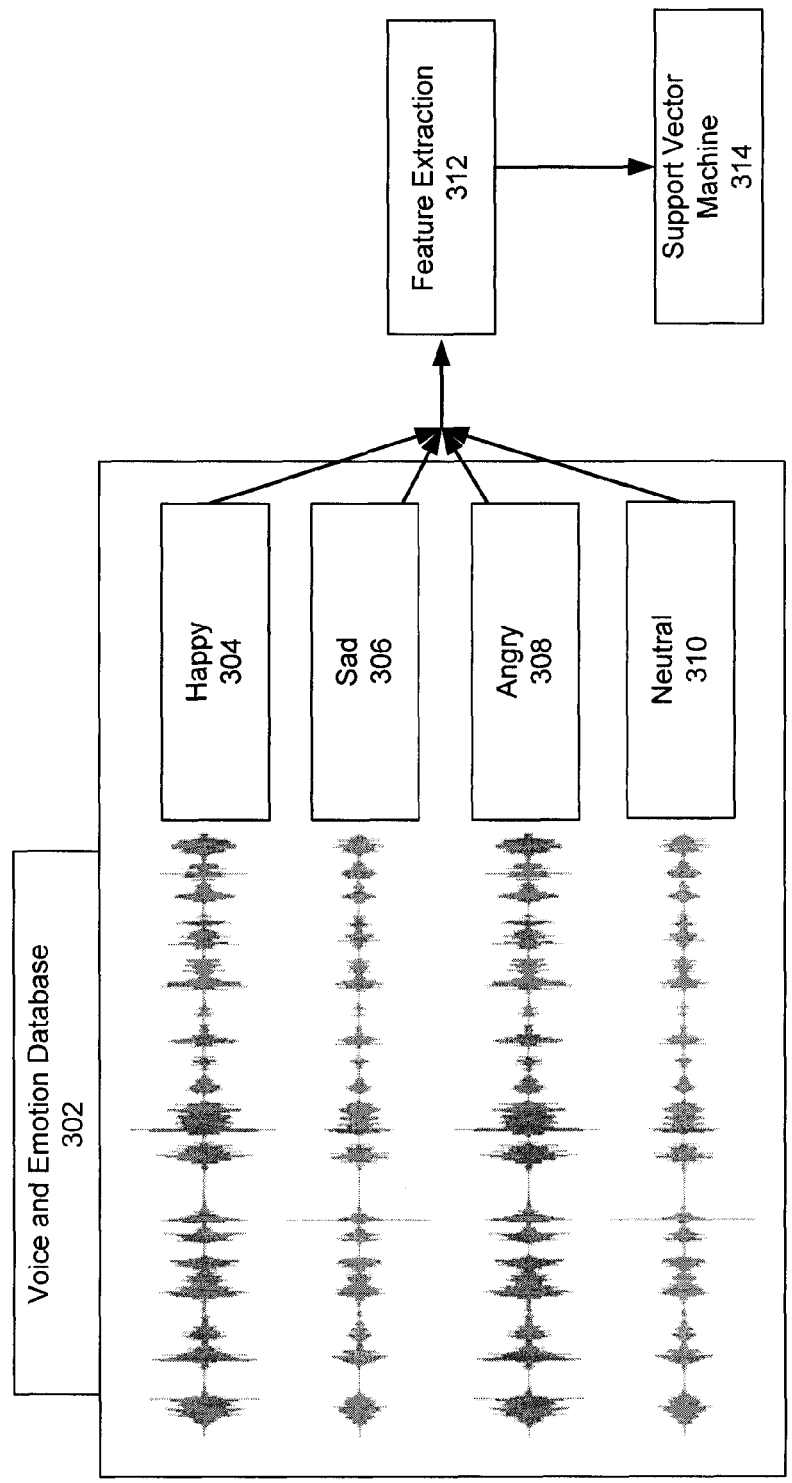
FIG. 3A depicts a training process for the algorithm in accordance with an exemplary embodiment.
Figure 3B:
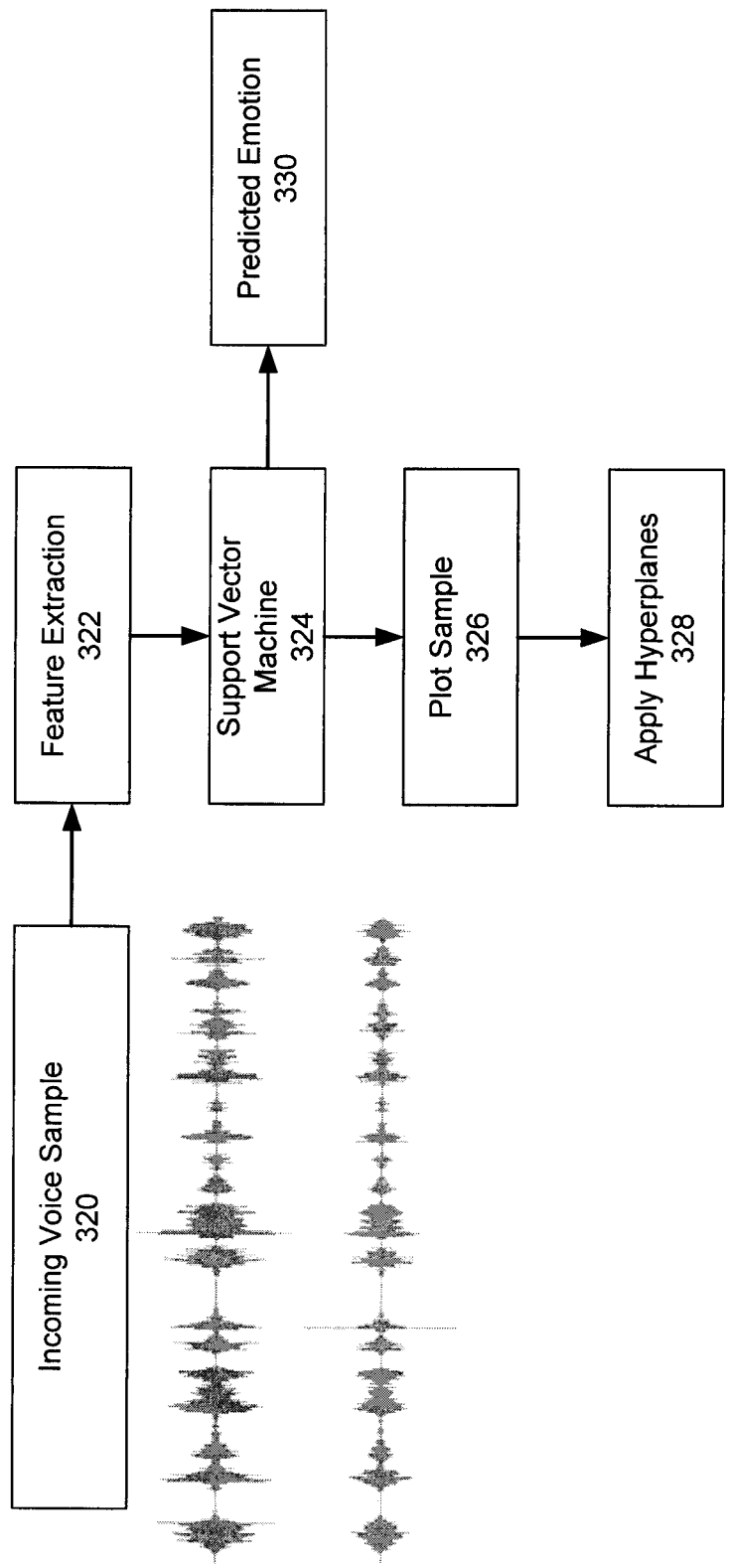
FIG. 3B depicts a process evaluating a real-time audio sample using the algorithm in accordance with an exemplary embodiment.

FIGS. 3A and 3B depict training the algorithm and evaluating a real-time audio sample, respectively.

As depicted in FIG. 3A, the algorithm may be trained using a high quality database 302 of sounds/audio samples. In the database development, according to exemplary embodiments, there were extracted a large number of two second sound bites from available media as well as recordings by the inventors. The database contents may be categorized. For example, the database contents may be characterized by emotional content of the sound bite such as happy 304, sad 306, angry 308, and neutral 310. It should be appreciated that these emotional categories may be expanded to include additional categories or sub-categories. In various embodiments, the sound bites may have meanings/definitions associated therewith. For example, the sound bites may consist of words/phrases. The meaning/definition that is appropriate for the associated emotional content may be stored in the database as described herein. In some embodiments, the database contents may be available via a website download. This wide availability enables crowdsourcing to be leveraged to further improve and expand the database contents. The database can serve as a learning tool for the system.

Feature extraction 312 may be performed on each sample in each category. For example, the feature extraction may include energy, pitch, and frequency composition. In various embodiments, over 380 features can be extracted from each audio sample. These features may represent the key characteristics that linguists have identified as the prominent features in voices. The feature extraction can serve to identify the key components of each type of emotional content of the audio sample. In various embodiments, a set of the most prominent characteristics of each type of emotional content may be identified and the feature extraction may focus on these prominent characteristics.

Regarding the over 380 features described above, there are 16 main features (or low-level descriptors) and each has a delta coefficient which is how each feature changes over time. There are 12 statistical parameters. Thus, there are a total of 16*2*12=384 features.

Providing further detail, the 16 low-level descriptors used may be: zero-crossing-rate (ZCR) from the time signal, root mean square (RMS) frame energy, pitch frequency (normalised to 500 Hz), harmonics-to-noise ratio (HNR) by autocorrelation function, and melfrequency cepstral coefficients (MFCC) 1-12 in accordance with Hidden Markow Model Toolkit (HTK)-based computation. To each of these, the delta coefficients are additionally computed. Next the 12 functional means, standard deviation, kurtosis, skewness, minimum and maximum value, relative position, and range as well as two linear regression coefficients with their mean square error (MSE) are applied on a chunk basis. Thus, the total feature vector per chunk contains 16*2*12=384 attributes. See http://emotion-research.net/sigs/speech-sig/emotion-challenge/INTERSPEECH-Emotion-Challenge-2009_draft.pdf, the contents of which are incorporated by reference.

Once these features have been characterized and quantified, the results can be fed into the algorithm. The SVM 312 may be trained by the audio samples in the database so that the SVM 312 can learn what various types of emotional content "look" like based on the characteristic. Following this, the emotional content of real-time samples can be determined using this learning by analyzing the characteristics of a real-time sample based on the learning from the database. In some embodiments, the database may be used for active comparison of real-time samples to samples in the database to find the closest emotional match.

FIG. 3B depicts the algorithm application to a real time audio sample in use. An incoming voice (audio) sample 320 is input into the algorithm. At 322, feature extraction is performed on the sample. The feature extraction may be as described above in FIG. 3A. The feature extraction may extract salient characteristics of the audio sample. The sample is then fed into a SVM 324. At 326, the parameters are plotted. At 328, hyperplanes are applied to the sample. The SVM outputs the predicted emotion at 330. Further details are provided below.

The algorithm breaks the task of emotion recognition in audio streams into two processes: feature extraction and data classification.

For example, for feature extraction, various algorithms and/or libraries may be used. For example, Python's PyAudio and Wave libraries can be used to record audio snippets in real-time and chunk them into data points based on a set time interval of two seconds. These data points may then be processed via OpenSMILE's (e.g., an open-source audio tool) feature extraction tools and then translated into feature vectors consisting of rational numbers corresponding to the selected features.

Upon being translated into feature vectors, the data is then classified by a SVM's classifier's predictive functionality, which generates an integer corresponding to the emotion of the audio snippet. This process then repeats continuously until the unit is powered off.

A SVM is a machine learning algorithm that serves as a classification method for various types of data. This machine learning algorithm works in two parts: first, a training part, and then a testing part. To train the SVM, a database of k-dimensional feature vectors is constructed from the audio samples and mapped into k-dimensional hyperspace. Hyperplanes are then drawn to optimally divide the hyperspace into the proper number of regions, which are labeled according to the already-classified data within that region. These hyperplanes are drawn in order to maximize the distance from the data points on the "edge" one set of categorized data to the "edge" of an adjacent set of categorized data. The construction of this hyperplane is dependent on the kernel function used by the SVM. As a result there are a number of functions that are optimal for different data classification tasks. For the purposes of emotion classification based on audio inputs, both the radial basis function (RBF) and cubic polynomial function have produced effective results.

For example, the SVM classifier used is a one vs. rest, cubic SVM that fits a classifier to each class of data (each type of emotion). The cubic/polynomial SVM is employed over the linear SVM due to its more desirable function space for multi-class classification and language processing. In various embodiments, the kernel used for classification may transition from a polynomial kernel to one based on the RBF. Furthermore, additional Naïve-Bayes classifiers may be added to the classification system in order to supplement the SVM classifications and mimic a random forest approach to classifications, with the mode of the classifications being output as the result instead of a result from a single classifier.

In calculating the closest emotional match, the SVM may give information about a percentage certainty. The information may be used internally as part of the algorithm processing. In some embodiments, the percentage certainty may be output by the SVM for review by the user. For example, as described above, the device may have a display screen. The percentage certainty may be output along with the emoticon graphic on the display screen for the user. These percentages can be used in minimizing random deviation/error in the SVM. For example, if the percentage certainty is not above a certain threshold, a slight change in emotion can be ignored and attributed to random error such as if the speaker is happy and has been detected to be happy for the past ten minutes, but the algorithm detects 30% certainty in sadness for two seconds, then that result is ignored due to the low certainty and the past detected emotions. Of course if the sadness persists in being detected, then it will not be ignored. This means that the algorithm will not just look at the classification results of the SVM, but will also consider and take into account previous outputs as well as percentage certainty in determining the given emotion. It should be appreciated that the preceding example is meant to be exemplary and non-limiting.

Various embodiments may use the SVM to improve social abilities of autistic children by coupling the SVM with word recognition software. This may be done in parallel with and/or in lieu of the embodiments described above. For example, this embodiment may use the embodiment as depicted in FIG. 1C to utilize the display output. The basic processing methodology may be as described above with the addition of word recognition software to provide an output containing the meaning or definition of the words and/or subtle nuances or unconventional definitions of the words from the conversation. In some embodiments, an appropriate response phrase may be output. These embodiments may leverage the database as described above such that not only is emotional content of the words/phrases (i.e., the sound bites) stored but also the meanings or definitions that are appropriate for the words/phrases corresponding to the emotional content. The device may have the word recognition software incorporated therein which may be communicatively coupled to the database and/or may have the word/phrase meanings stored therein to pair them with the determined emotional content of the audio sample (i.e., the words/phrases detected).

An issue that is observed with children having ASDs is that they are slow in understanding many social and traditional events and activities that persons without ASDs partake in without much thought. In the various embodiments described above, the emotional state of the speaker may be determined, however, there is more information that could be transmitted to the user. For example, the phrase "shut up" has many meanings to vary based on the tone used by the speaker. With a low, serious and/or sad tone, the phrase may show anger, disapproval, and disagreement. With a happy, vibrant and high energy tone, the phrase may be used in a joking manner to show surprise and even congratulations. To some children with ASDs who are capable of language and know the formal definition, but not the colloquial one that may be used by certain speakers, such a phrase used in a conversation could be shocking to these children. As a further example, more serious and extreme phrases, such as "you're dead" or "this project is killing me" or "I'm going to kill you," can carry dark and violent meanings if projected incorrectly, and could be actual sources of concern and discomfort for some children with ASDs, depending upon their functional level. Thus, coupling the emotional state with the word/phrase meaning that is appropriate may be beneficial and useful. For example, an output may be provided that provides not only the emotional content of the speech (which can be output as described above) but also an appropriate meaning of the words/phrase that couples with the emotional content. More than one meaning may be provided. This output may be provided on a display associated with the device.

It should also be appreciated that certain popular phrases that are commonly used, such as "let us pray" and "we mourn the death of . . . ," typically carry archetypal meanings and may be sources of lessons for young children with ASDs who are just beginning to learn social norms, etiquettes, rituals and activities. For example, when the phrase "congratulations" is detected, the display may indicate that typically, people show respect and gratitude when receiving praise or an award as a definition. As a second example, when the phrase "you are not going to believe what happened today" is used, the output may inform the user to ask the other person to inquire about their situation, prompting them with phrases like, "what happened?" or "what's going on?" Thus, the output can not only provide a definition to provide situational awareness of what is going on but may also provide a response phrase to help guide the user in the conversation. Word recognition may therefore provide a broad spectrum of opportunities for children with ASDs, as well as adults with ASDs, to engage in meaningful conversations assisted by exemplary embodiments.

In various embodiments, minimizing background noise may be important and, according to exemplary embodiments, background noise may be handled by using percentage certainties (as described above), modes, and a noise filter.

Various embodiments may use a neural network. A neural network method may be ideal for emotion detection within voice samples given its ability to address pattern recognition problems such as described herein. The algorithm rapidly assays signal data via a multi-factor analysis approach. The input to the network is the pitch mean, pitch variance, number of accented syllables, and a Boolean reporting whether the last syllable is accented. Each of the non-Boolean inputs have a maximum integer threshold N, and log(N) neurons are allocated towards these inputs. The output level of the network contains two neurons (two bits of information), enough to cover the four output emotions: happy, angry, sad, and neutral. The network is a feed-forward network with back-propagation primed to work efficiently for specific users and successive uses. Prior to implementing this network method in the bracelet, the emotion database was developed through recordings of emotive voice to train the algorithm to optimum accuracy and efficiency. In subsequent versions, there was incorporated extraction of pitch contours within larger speech segments and increase the number of emotional signatures. The neural network may be used in addition to or in lieu of the algorithm described above.

Figure 4A:
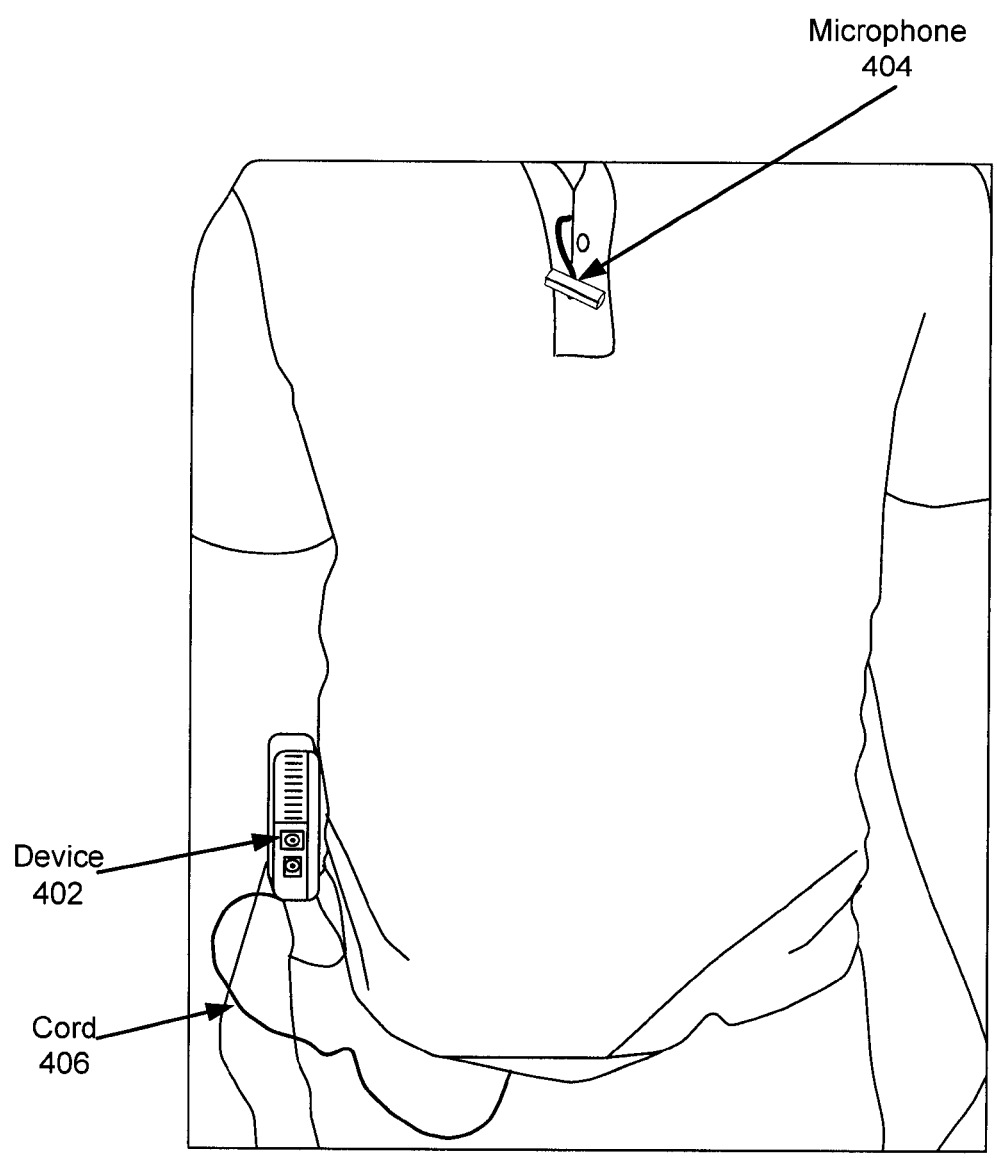
FIG. 4A depicts an individual wearing a visible device in accordance with an exemplary embodiment.

FIG. 4A depicts an individual wearing a visible device in accordance with an exemplary embodiment. This depiction is meant to be exemplary and non-limiting. An individual 400 may have a device 402 with an external microphone 404 mounted on their person. As depicted in FIG. 4A, the device 402 may be clipped on the belt or pants of the individual 400. The device 402 may be mounted in other positions or locations on the person 400. For example, while the device 402 is depicted in FIG. 4A as being worn on the right hip (mounted on a belt) of the individual, various embodiments may include a wrist-mounted device or a device worn on an arm-band or may be mounted on the other hip or even in the posterior area of the person 400. Additionally, the device 402 is depicted as having a transparent case. In various embodiments, the case of the device 402 may be opaque and have a particular color. Furthermore, it should be appreciated that while the device 400 is depicted as being a particular size and having a particular configuration, other sizes and configurations are possible. For example, the device may be smaller and may lack the ports depicted in FIG. 4A or may have a differing port configuration.

The microphone 404 may be clipped to a shirt as depicted. The microphone 404 may be connected to the device 402 with a cord 406. As depicted, the cord 406 may be partially concealed beneath the shirt of the individual 400. It should be appreciated that in various embodiments, the microphone 404 may be wirelessly coupled to the device 402, obviating the need for a cord. In other embodiments, the microphone 404 may be integrated into the device 402. Furthermore, the microphone 404 may be of a different size and shape in various embodiments. It should be appreciated that the microphone should be located and oriented such that it can best capture audio from a person or person(s) speaking to or near the individual 400.

Figure 4B:
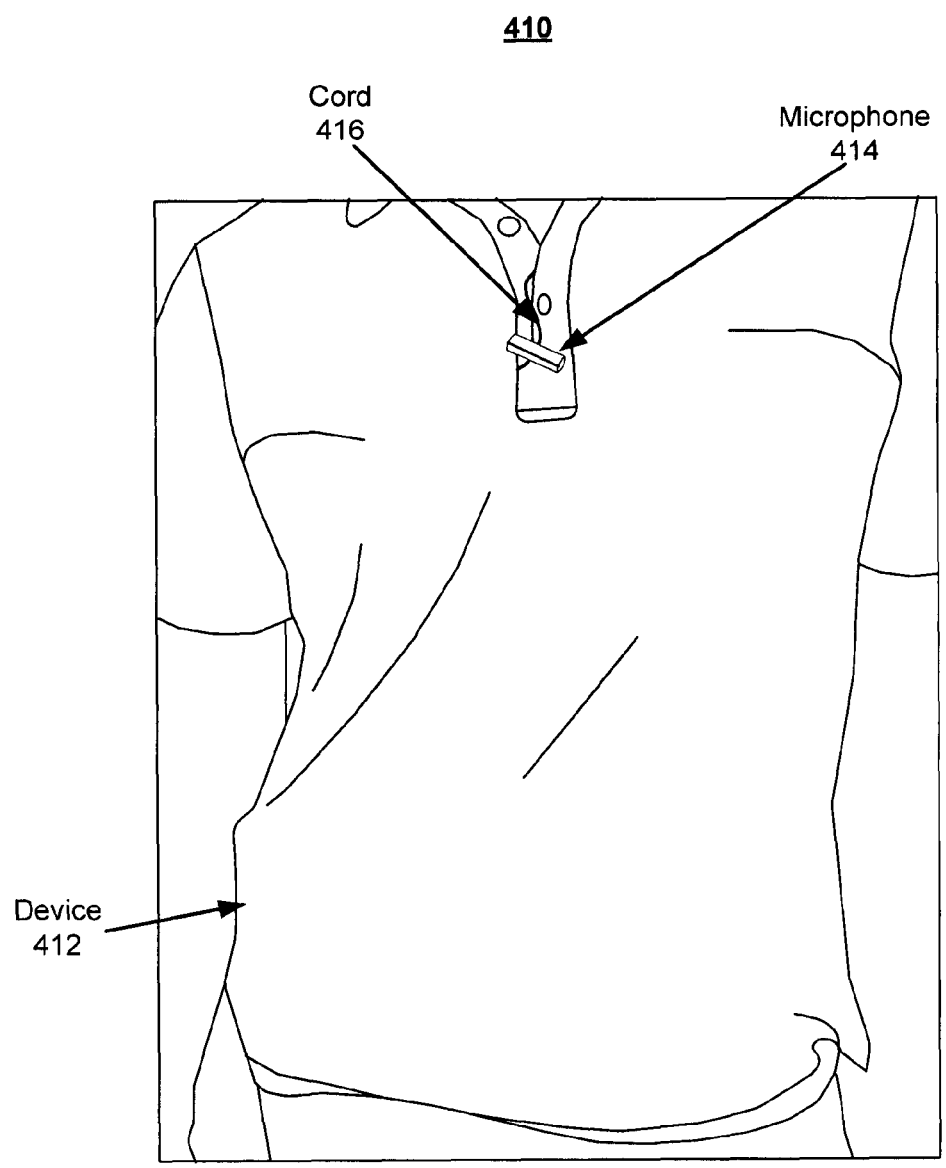
FIG. 4B depicts an individual wearing a concealed device in accordance with an exemplary embodiment.

FIG. 4B depicts an individual wearing a concealed device in accordance with an exemplary embodiment. This depiction is meant to be exemplary and non-limiting. An individual 410 may have a device 412 with an external microphone 414 mounted on their person. As depicted in FIG. 4B, the device 412 may be concealed. For example, the device may be concealed under clothing as depicted. In various embodiments, the device 400 may be located in a pocket or placed inside of a waistband of pants (for example). The device 412 may be mounted in other positions or locations on the person 410. For example, while the device 412 is depicted in FIG. 4B as being concealed on the right hip (mounted on a belt and covered by a shirt) of the individual, various embodiments may be mounted on the other hip or even in the posterior area of the person 400 and so concealed.

The microphone 414 may be clipped to a shirt as depicted. The microphone 414 may be connected to the device 412 with a cord 416. As depicted, the cord 416 may be concealed beneath the shirt of the individual 410. It should be appreciated that in various embodiments, the microphone 414 may be wirelessly coupled to the device 412, obviating the need for a cord. In other embodiments, the microphone 414 may be integrated into the device 412. Furthermore, the microphone 414 may be of a different size and shape in various embodiments. It should be appreciated that the microphone should be located and oriented such that it can best capture audio from a person or person(s) speaking to or near the individual 410.

Figure 5:
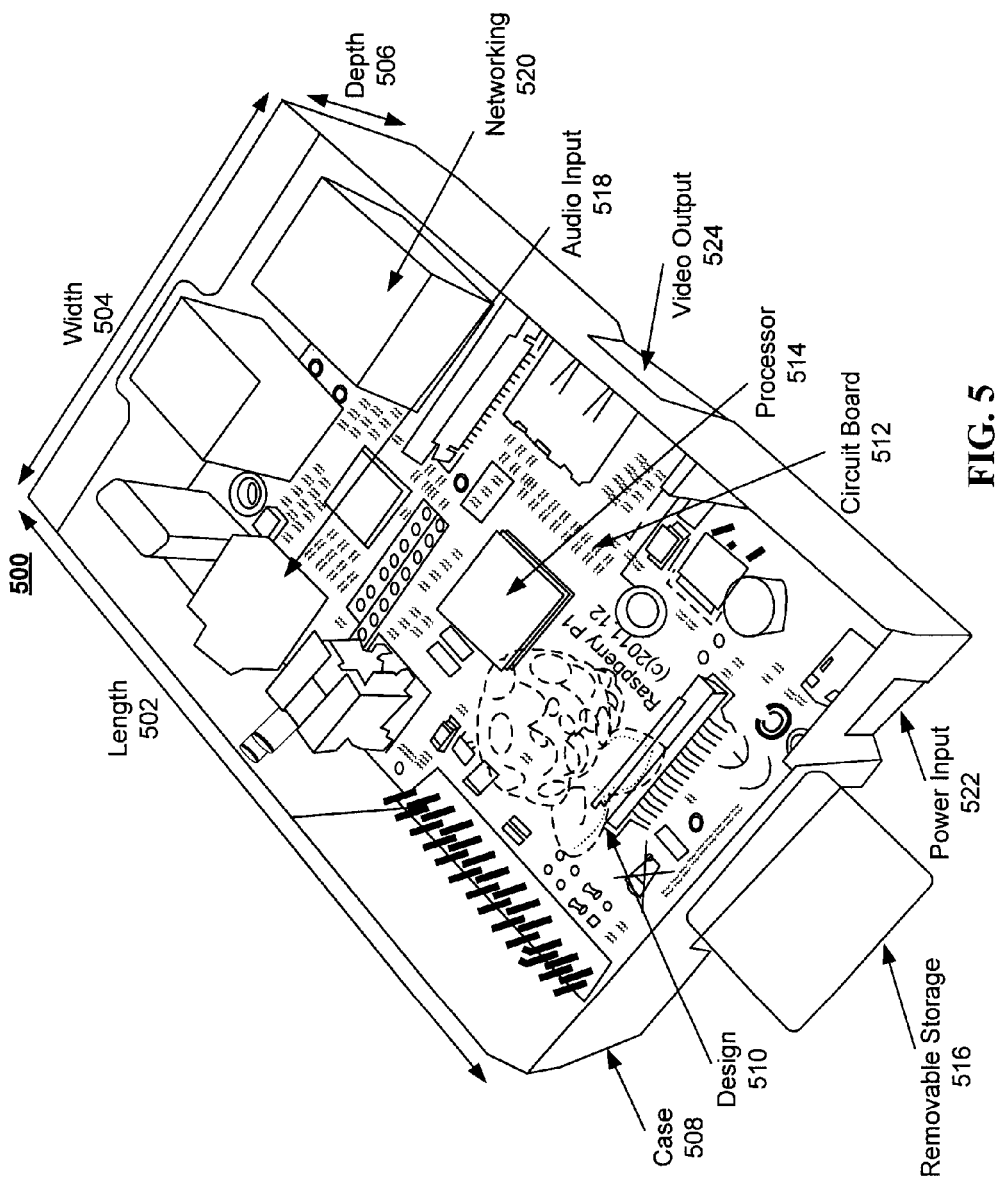
FIG. 5 depicts a device in accordance with an exemplary embodiment.

FIG. 5 depicts a device in accordance with an exemplary embodiment. The device 500 may include components as described herein, such as, for example, in FIGS. 1A-1C. The device 500 may be the same as the device 402 depicted in FIG. 4A. The device 500 may be of various sizes. According to various embodiments, the device 500 may be the size of a standard credit card in length 502 and width 504 with a slightly greater depth. For example, the device 500 may be a Raspberry Pi type device. It should be appreciated that the device 500 is meant to be exemplary and non-limiting.

The device 500 may have a transparent case 508. In various embodiments, the case 508 may be opaque and be of a various color. For example, the case 508 may be black. The case 508 may have a logo 510 or other design or artwork thereon. The design 510 may be imprinted into the case 508 or may be placed upon the surface of the case 508 (internally or externally). The case 508 may be openable to allow access to the internal components. This access may allow for the replacement and/or upgrade of components. The case 508 may include a lock or other mechanism to prevent unauthorized access or opening of the case. In a similar manner, the components of the device 500 may be mounted together such that the components are replaceable as a single unit and could be removed together and transferred to a new case. In various embodiments, individual components may be replaceable.

The device 500 may have a circuit board 512. The circuit board 512 may be a motherboard type circuit supporting at least one computer processor, computer memory (transitory and non-transitory, both internal and external), and various ports/connections. The circuit board 512 may include connections, heat sinks/heat exchangers, and other electronic and electrical components required for the functioning of the device 500. The components of the circuit board 512 may be individually replaceable for repair and/or upgrade and/or replacement. In various embodiments, the device 500 may include a processor 514. The processor 514 may include a central processing unit, a graphics processing unit, and a sound processing unit/card, as well as computer memory. The device 500 may include removable storage 516. The removable storage 516 may be in the form of a memory card. For example, the memory card may be a flash storage or solid state storage card or device. The device 500 may include an audio input 518. The audio input 518 may be the coupling point for the microphone, as described above. In some embodiments, an external sound card (not shown) may be coupled thereto and the microphone coupled to the external sound card. A networking capability 520 may be provided. This may enable the device 500 to be communicatively coupled to a computer or a computer based network. The coupling may be hard wired or wireless according to various embodiments. The device 500 may include a power input 522. The power input 522 may enable a battery or other power source to be operatively coupled to the device 500. The coupling may be through a cable, such as a USB type cable. In some embodiments, the battery or other power source may be internal to the device 500 (that is, contained within the case 500). The device 500 may have a video output 524. The video output 524 may enable a video signal to be output to an external display. The video output 524 may be a RCA or USB or HDMI or DVI type connection. However, it should be appreciated that other types of video output connections are possible.

While the embodiments have been particularly shown and described within the framework of the exemplary embodiments, it will be appreciated that variations and modifications may be effected by a person of ordinary skill in the art without departing from the scope of the invention. Furthermore, one of ordinary skill in the art will recognize that such processes and systems do not need to be restricted to the specific embodiments described herein. Other embodiments, combinations of the present embodiments, and uses and advantages of the present invention will be apparent to those skilled in the art from consideration of the specification and practice of the invention disclosed herein. The specification and examples should be considered exemplary.

What is claimed is:

1. A computer implemented method, comprising:
   receiving, by a computer processor, an audio input from a first person comprising spoken words;
   sampling, by the computer processor, the audio input into a sample of a predetermined length of time;
   receiving, by a support vector machine, the sample;
   applying, by the support vector machine, an algorithm to the sample;
   determining, by the support vector machine, an emotional content of the sample by accessing a database comprising audio samples with predetermined emotional content and determining the closest emotional match to the sample from the predetermined emotional content such that the determining the closest emotional match trains the algorithm to optimize accuracy in determining the closest emotional match for subsequent samples; and
   outputting, by the support vector machine, the closest emotional match to the emotional content of the sample for use by a second person having an autism spectrum disorder.

2. The method of claim 1, wherein the computer processor is contained in a wearable device.

3. The method of claim 2, wherein the wearable device is worn by the second person having an autism spectrum disorder.

4. The method of claim 3, wherein the outputting comprises a vibratory pattern that corresponds to the closest emotional match and the vibratory pattern is felt by the second person.

5. The method of claim 3, wherein the wearable device is a bracelet.

6. The method of claim 3, wherein the outputting comprises an output on a display of the wearable device.

7. The method of claim 1, wherein the computer processor is part of a portable computing device.

8. The method of claim 1, wherein the audio input is received through a microphone.

9. The method of claim 1, wherein the vibratory pattern comprises four different patterns corresponding to neutral, happy, sad, and angry emotions.

10. The method of claim 1, wherein the output is further used as a training tool for the second person having an autism spectrum disorder to learn to recognize emotional content of spoken words through leveraging of neural plasticity.

11. The method of claim 1, wherein the output further comprises word recognition technology, in the context of the detected closest emotional match, to output additional information regarding content of the spoken words from the audio input.

12. A non-transitory computer readable medium storing an executable program comprising instructions to perform the method of claim 1.

13. An apparatus, comprising:
    a wearable device, comprising:
       a processor;
       a support vector machine; and
       a memory comprising computer-readable instructions which when executed by the processor cause the processor and the support vector machine to perform the steps comprising:
          receiving an audio input from a first person comprising spoken words through a microphone communicatively coupled to the processor;
          sampling the audio input into a sample of a predetermined length of time;
          applying by the support vector machine an algorithm to the sample;
          determining, by the support vector machine, an emotional content of the sample by accessing a database comprising audio samples with predetermined emotional content and determining a closest emotional match to the sample from the predetermined emotional content such that the determining the closest emotional match trains the algorithm to optimize accuracy in determining the closest emotional match for subsequent samples; and
          outputting, by the support vector machine, the closest emotional match to the emotional content of the sample for use by a second person having an autism spectrum disorder.

14. The apparatus of claim 13, wherein the wearable device is worn by the second person having an autism spectrum disorder.

15. The apparatus of claim 14, wherein the outputting further comprises a vibratory pattern that corresponds to the closest emotional match and the vibratory pattern is felt by the second person.

16. The apparatus of claim 14, wherein the wearable device is a bracelet.

17. The apparatus of claim 14, wherein the outputting comprises an output on a display of the wearable device.

18. The apparatus of claim 13, wherein the vibratory pattern comprises four different patterns corresponding to neutral, happy, sad, and angry emotions.

19. The apparatus of claim 13, further comprising: a database comprising audio samples with predetermined emotional content.

20. The apparatus of claim 19, wherein the algorithm determines a closest emotional match to the emotional content based on training by the database.

21. The apparatus of claim 20, wherein the wearable device and the database are communicatively coupled over the Internet or a cloud-based computer network.

22. The apparatus of claim 13, wherein the processing is performed remotely from the wearable device over the Internet or a cloud-based computer network.

23. The apparatus of claim 13, wherein the output further comprises word recognition technology, in the context of the detected closest emotional match, to output additional information regarding content of the spoken words from the audio input.

24. A computer implemented method for determining emotional content of an audio sample, comprising:
- performing feature extraction of the audio sample, the audio sample comprising an audio input from a first person comprising spoken words;
- receiving, by a support vector machine, the audio sample;
- plotting parameters of the audio sample,
- applying hyperplanes to the audio sample,
- predicting the emotional content of the audio sample, based on previous learning by the support vector machine using previously extracted audio samples characterized by emotional content; and
- outputting, by the support vector machine, the predicted emotional content of the audio sample for use by a second person having an autism spectrum disorder.

* * * * *